United States Patent
Aghassi et al.

(10) Patent No.: US 6,649,368 B1
(45) Date of Patent: *Nov. 18, 2003

(54) COMPOSITION AND METHOD FOR TREATING TISSUE SAMPLES

(75) Inventors: Nora Betyousef Aghassi, Hot Spring, AR (US); Kim Franceschini, Austin, TX (US); Paul John Ardi, Hot Springs Village, AR (US)

(73) Assignee: Cell Marque Corporation, Hot Springs, AR (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 195 days.

(21) Appl. No.: 09/515,283

(22) Filed: Feb. 29, 2000

Related U.S. Application Data

(63) Continuation-in-part of application No. 08/957,098, filed on Oct. 24, 1997, now abandoned.

(51) Int. Cl.$^7$ ..................... G01N 33/53; G01N 33/543; G01N 33/567
(52) U.S. Cl. .................. 435/40.52; 435/5; 435/7.1; 435/7.2; 435/7.21; 435/7.32; 435/7.94; 435/7.95; 435/40.5; 436/503; 436/518
(58) Field of Search ............... 435/40.5, 40.52, 435/7.1, 7.94, 7.95, 7.25, 7.28, 7.32

(56) References Cited

U.S. PATENT DOCUMENTS

| | | | | |
|---|---|---|---|---|
| 5,252,246 A | * | 10/1993 | Ding et al. | 510/137 |
| H1478 H | * | 9/1995 | Prieto | 510/340 |
| 5,552,294 A | * | 9/1996 | Thorne | 435/7.32 |
| 5,856,289 A | * | 1/1999 | Kennedy | 510/365 |

FOREIGN PATENT DOCUMENTS

| | | |
|---|---|---|
| WO | 94/04906 * | 3/1994 |

OTHER PUBLICATIONS

Yorukoglu et al. Epitope retrieval technique: a simple modification that reduces staining time. Applied Immunohistochemistry 5(1): 71, 1997.*

Shi et al. Antigen retrieval immunohistochemistry under the influence of pH using monoclonal antibodies. J. Histochem. Cytochem. 43(2): 193–201, 1995.*

Hazelbag et al. Immunostaining of chain–specific keratins on formalin–fixed, paraffin–embedded tissues: a comparison of various antigen retrieval systems using microwave heating and proteolytic pre–treatments. J. Histochem. Cytochem. 43(4): 429–437, 19, 1995.*

Norton et al. Brief, high–temperature heat denaturation (pressure cooking): a simple and effective method of antigen retrieval for routinely processed tissue. J. Pathol. 173: 371–379, 1994.*

Miller et al. Heat–induced epitope retrieval with a pressure cooker: suggestions for optimal use. Applied Immunohistochem. 3(3): 190–193, 1995.*

Cattoretti et al. Antigen unmasking on formalin–fixed, paraffin–embedded tissue sections. J. Pathol. 171: 83–98, 1993.*

Cell Marque Corporation, 1998. "Immuno Pathology 1998 Products and Reference Guide" (K. Franceshini, ed.). pp. 2, 3, and 45.*

* cited by examiner

*Primary Examiner*—Christopher L. Chin
*Assistant Examiner*—James L. Grun
(74) *Attorney, Agent, or Firm*—Jackson Walker LLP

(57) ABSTRACT

Compositions and methods are described for enhancing the immunohistochemical staining of tissue samples. Compositions include a single solution, which includes at least one surfactant, adapted to remove an embedding medium of a tissue sample, rehydrate the tissue sample, and enhance the immunohistochemical staining of the tissue in relation to immunohistochemical staining of unreacted tissue. Methods include heating the tissue sample with the composition to enhance the immunohistochemical staining of the tissue.

12 Claims, No Drawings

COMPOSITION AND METHOD FOR TREATING TISSUE SAMPLES

The present invention is a continuation-in-part and claims priority on U.S. patent application Ser. No. 08/957,098 filed Oct. 24, 1997, now abandoned.

BACKGROUND OF THE INVENTION

1. Field of Invention

The present invention generally relates to the enhancement of immunohistochemical staining of fixed tissue samples. More particularly, an embodiment of the invention relates to the enhancement of immunohistochemical staining of embedded formalin-fixed tissue samples using a single composition in a single step.

2. Description of Related Art

Tissue sections obtained from clinical or animal experimentation frequently have been fixed, embedded and stored in a form suitable for later examination by microscopy. Traditional fixation methods frequently have employed aldehyde fixatives, which fix the tissue by causing cross-linking reactions within and between tissue proteins. Cross-links tend to preserve tissue morphology and integrity, harden the tissue for slicing, and inhibit microbial attack. After tissue samples have been fixed, they are typically embedded in an embedding medium so that the samples may be cut into thin sections. Paraffin is the most common embedding medium, although acrylamide and celloidin may also be used.

Aldehyde fixation tends to cause substantial changes to the structure of the tissue sample. These changes often tend to cause the antigens that may be present in the tissue samples to lose their reactivity toward antibodies that target such antigens. One effect of formalin fixation is to substantially lock the three dimensional shape of protein molecules within the tissue samples. Because of the recent development of new immunohistochemical reagents, immunohistochemical analyses may now be performed that were impossible to perform at the time many tissues were originally stored. Therefore, a number of procedures have been developed which could reverse some of the changes produced by aldehyde fixation, and enhance the immunohistochemical staining properties of the tissue sample.

One method for improving the staining abilities of tissue samples which have been fixed in formalin and embedded in acrylamide gel relates to treatment of acrylamide gel embedded tissue in 1.0% 2-mercaptoethanol for 15 minutes, followed by rinsing with phosphate buffered saline. This treatment allowed the tissue samples to be stained by a number of staining reagents. A method for restoring the imnunohistochemical staining properties of tissue samples is described in U.S. Pat. No. 5,244,787 to Key et al. This method involved removing the embedding medium in a pretreatment step. For Paraffin-embedded tissue samples, this pretreatment was accomplished by e clearing the tissue samples in xylenes and rehydrating the samples. After the embedding medium has been removed, the sample may be heated in either de-ionized water, an aqueous solution of a zinc salt, or an aqueous solution of a lead salt. The tissue samples were reported to show improved immunohistochemical staining properties when heated in a microwave oven. Improvement was reportedly seen when the solution was heated to its boiling temperature. In general, microwave heating appears to have been found by Key et al to give better results than conventional heating. Solutions containing zinc or lead salts apparently gave significantly better results than de-ionized water.

Another method for restoring the immunohistochemical staining properties of tissue samples is described in U.S. Pat. No. 5,578,452 by Shi et al. In this method the formalin-fixed embedded tissues were treated with a solution of an aldehyde releasing reagent. The aldehyde releasing reagent may release aldehyde from the tissue sample by reacting with the aldehyde in a substantially irreversible manner to form a non-aldehyde derivative.

A number of investigators have investigated the importance of several reaction conditions with respect to enhancement of immunohistochemical staining ability. In general it has been found that the pH of the solution and temperature tend to have the most effect on the staining ability of the tissue samples. In general, with some limitations, the higher the temperature during the enhancement of the tissue samples, the better the staining enhancement tends to be. The effect of pH tends to be dependent on the type of antibody being used in the staining process and may be optimized for the antibodies to be used during the staining procedure.

The above mentioned methods inadequately address, among other things, the restoration of paraffin embedded tissue samples in a single reaction step. The procedures described above are usually performed on deparaffinized samples. Typically, the paraffin embedding medium is removed from the samples by successive immersion through a series of xylenes. Following removal of the paraffin embedding medium, the tissue must then be rehydrated by treatment with a series of ethanol-water solutions ranging typically from 100% ethanol to 90% ethanol. Finally, after the sample is rehydrated, the sample must be treated with a solution to reverse the effects of formalin fixation a step known as unmasking. It is therefore desirable that a single solution be provided that allows the steps of deparaffination (or de-embedding), rehydration, and unmasking of embedded tissue samples to be combined.

SUMMARY OF THE INVENTION

An embodiment of the invention relates to a liquid composition for enhancing the immunohistochemical staining ability of tissue samples. The composition preferably includes an aqueous solution of a removing agent and a tissue activating agent. The composition preferably substantially simultaneously: (i) removes the embedding medium from the tissue; (ii) improves immunohistochemical staining of the tissue in comparison to tissue that has not been contacted with the composition; and (iii) substantially hydrates the tissue. The removing agent is adapted to substantially remove an embedding medium from a tissue sample. The removing agent is preferably an emulsifier, more preferably a surfactant. The removing agent preferably includes one or more of an amphoteric, anionic, cationic, or nonionic surfactant. The tissue activating agent is adapted to alter the morphology of a component of the tissue sample. The tissue activating agent preferably includes a buffering agent or a metal salt. The pH of the composition is preferably adjusted to lie between 5 to 10 by addition of an acid or base.

In another embodiment the composition preferably includes an aqueous solution of SIMPLE GREEN. Simple Green has been described in U.S. Pat. No. 5,856,289 as: by weight about 5.8% ethylene glycol monobutyl ether, about 3.75% nonylphenol ethoxyate, about 1.5% tetrapotassium pyrophosphate and about 88.95% water. SIMPLE GREEN is a non-toxic, biodegradable, environmentally safe detergent concentrate which may provide a mixture of emulsifiers. The composition may include a buffering agent. The pH of the solution is preferably adjusted to lie between 5 and 10 by addition of an acid or a base. The composition preferably substantially simultaneously: (i) removes the embedding medium from the tissue; (ii) improves immunohistochemical staining of the tissue in comparison to tissue that has not been contacted with the composition; (iii) substantially hydrates the tissue.

In another embodiment of the composition the removing agent includes aqueous solutions of at least one of the following emulsifiers, including detergents and surfactants: Igepal-630 (sigma #3021); Tween 20 (sigma #P7949); Brij 35 (sigma #P 1254); Brij 90 (sigma #P 1254); Triton X-100 (sigma #T9284); CD TAB (sigma #C5335); and Tween 80 (sigma #P8074). Reference to "sigma"is reference to ©1999 Sigma—Aldrich catalog entitled: "Biochemicals and Reagents for Life Science Research", which is incorporated herein by reference.

The composition is preferably used to enhance the immunohistochemical staining of the tissue sample. In a preferred method the tissue samples are cut into sections of less than 5 microns. The tissue samples may be mounted on a positively charged slide. The sections are preferably dried at about 58° C. for one hour. After this time the samples are preferably submersed within the composition. The tissue samples are preferably heated to a temperature of about 120° C. at a pressure of about 10 p.s.i. for about 10–15 minutes. After heating the tissue samples are preferably placed in a container containing unused composition at a temperature of at least 90° C. for up to about 5 minutes. The tissue sample may be washed with an aqueous solution of a buffering agent before staining. An advantage of the present invention relates to the use of a single composition, in a single step, to enhance the immunohistochemical staining ability of tissue samples.

Another advantage of the present invention is that the sample may be used on Paraffin-embedded tissues without removing the paraffin embedding medium prior to treatment. Yet another advantage of the present invention is to provide a non-toxic, biodegradable composition for pretreatment of slides. Yet another advantage of the present invention is that the composition preferably substantially simultaneously: (i) removes the embedding medium from the tissue; (ii) improves immunohistochemical staining of the tissue in comparison to tissue that has not been contacted with the composition; and (iii) substantially hydrates the tissue.

DETAILED DESCRIPTION OF THE PREFERRED EMBODIMENTS

Tissue sections obtained from clinical or animal experimentation frequently are fixed, embedded and stored in a form suitable for later examination by light microscopy. Traditional fixation methods frequently have employed aldehyde fixatives, especially formaldehyde, which preserves the integrity of the tissue samples as well as protects the sample from microbial attack. Tissue antigens tend to be masked, that is, the antigens within the tissue are no longer reactive toward antibodies. When aldehyde based fixatives are used, this masking of the antigens is thought to be due to the reaction of the aldehyde with the tissue proteins. During the fixation process, the aldehyde presumably fixes the tissue by causing cross-linking reactions within and between tissue proteins, as well as causing other unknown changes to the tissue structure. These cross-links within the tissue proteins tend to alter the three dimensional shape of the protein, preventing access of antibodies to the antigens.

After tissue samples have been fixed, they are typically embedded in an embedding medium, such as paraffin or celloidin, so that the samples may be cut into thin sections. The embedding process is preferably accomplished by soaking the tissue samples within the embedding medium such that the tissue samples are substantially surrounded by the embedding medium. In many cases the embedding medium may also soak into the interior of the tissue samples. The embedding medium may prevent the tissue samples from being stained during an immunohistochemical staining procedure.

Recently, new techniques in immunohistochemical staining of tissue samples have been developed. In general tissue samples are studied for the presence of different types of cells. The specific type of cells being studied may be stained, in the presence of other cells, by the application of immunohistochemical staining techniques. During an immunohistochemical staining process the tissue sample may be reacted with an antibody which specifically binds with the type of cells being studied, and no other type of cells. The bound cell-antibody complex may now be stained, without staining any of the other cells, to allow the stained cells to be easily distinguished from the other cells in the tissue sample. These techniques typically require the antigens to be unmasked before use. Because of the wide spread use of formaldehyde as a fixation chemical or a constituent thereof, it is desirable to provide a procedure whereby the antigenic activity of these tissue samples may be restored. Such a procedure may also take into account the embedding medium of the tissue samples. Formalin-fixed tissue samples are commonly embedded in paraffin before use. Removal of a portion of the embedding medium is thought to be necessary before immunohistochemical staining may be accomplished.

The enhancement of immunohistochemical staining of embedded, fixed tissue samples (typically formalin-fixed tissue samples) may be achieved by treating the tissue samples with an appropriate liquid composition. The composition preferably improves the staining of the tissue samples by accomplishing three effects. These effects may be accomplished substantially simultaneously. First, the composition may substantially remove the embedding medium from the tissue sample. Removal of the embedding medium allows the penetration of the immunohistochemical stains into at least a portion of the tissue samples preserved by the fixation process. Finally, the composition preferably rehydrates the tissue sample. During the process of fixation most of the water is removed from the tissue sample, rehydration of the tissue sample may allow the tissue to change its morphological structure and/or attain its original morphological structure.

An embodiment of a liquid composition for enhancing the immunohistochemical staining ability of embedded tissue samples includes a removing agent and a tissue activating agent. The composition may be a solution of the removing agent and the tissue activating agent in a solvent. The composition preferably is an aqueous solution of the removing agent and the tissue activating agent. The removing agent is preferably adapted to substantially remove an embedding medium from the tissue sample. During the process of embedding, the tissue becomes substantially surrounded with the embedding medium such that the embedding medium may inhibit the tissue from reacting with antibodies. To enhance the immunohistochemical staining of the tissue samples, at least a portion of the embedding medium is preferably removed from the tissue sample. To achieve the best results it is preferred that substantially all of the embedding medium is removed.

In some cases the embedding medium may be substantially water soluble. In this case water may act as the removing agent as well as a solvent for the tissue activating agent. If the embedding medium is a non-polar medium, such as paraffin, and the composition is an aqueous solution, the removing agent may induce the formation of an emulsion of the embedding medium within the composition. The term "emulsion" within the context of this application is taken to mean a stable mixture of two or more immiscible liquids held in suspension. The mixture may be held in suspension by one or more surfactants. An elevated temperature may be necessary to maintain such suspension.

The removing agent is preferably a surfactant. A surfactant is any compound that reduces the interfacial tension between two liquids or between a liquid and a solid. In general surfactants allow a solid or liquid, normally immiscible with a solvent, to become finely suspended with the solvent. Surfactants are typically divided into four classes: amphoteric, anionic, cationic, and non-ionic. The removing agent may be taken from any of these classes of surfactants. Preferably, the removing agent may be comprised of a mixture of compatible surfactants taken from one or more of these classes.

Nonionic surfactants include molecules that contain a substantially polar functional group attached to a substantially non-polar group.

The tissue activating agent is preferably adapted to interact with the tissue sample such that the morphology of the components of the tissue are altered. In general the tissue sample contains a number of biological components, including proteins and nucleic acids. Each of these components have a specific three dimensional structure related to the composition of the component. During the fixation, the tissue sample may be treated with an aqueous solution of formaldehyde. The formaldehyde reacts with the components to alter the three dimensional shape of these components, i.e. alter the morphology. These alterations tend to make the tissue samples substantially unreactive toward various immunohistochemical staining protocols. The tissue activating agent is preferably adapted to further alter the morphology of the tissue samples, such that the tissue samples are more reactive toward immunohistochemical reagents. While the tissue activating reagent restores some of the reactivity of the tissue samples, it may not be necessary that the tissue be restored to its original morphology to increase the reactivity of the samples toward immunohistochemical stains.

A number of metal salts may be used as a tissue activating agent. Salts useful in the composition include, but are not limited to: aluminum chloride, sodium chloride, sodium fluoride, iron chloride, zinc sulfate, and lead thiocyanate. In general aqueous solutions containing these and other metal salts improve the immunohistochemical staining ability of tissue samples to a greater extent than de-ionized water. It is believed that these salts may exert an effect on the morphology, i.e. three dimensional shape, of the protein components. The interaction of these salts with the protein molecule may aid in allowing the protein to attain a substantial part of its original three dimensional shape.

Chelators may be used as tissue activating agents. These chelators include: EDTA (sigma #E9884); EGTA (sigma #E4378); CDTA (sigma #D0922); EDADP-X (sigma #E1254); EDADP-B (sigma #E2004); EDDRA (sigma #E4135); DFA: (sigma #D9533); PPi (sigma #P8010); EDTP-B and EDTP-X. Of these, the preferred chelators are EDDHA, EDTA and EGTA. The concentration of these chelators as tissue activating agents is preferably in the range of 1 to 2 millimolar.

Buffering agents may also be used as a tissue activating agent. Buffering agents useful in the composition include, but are not limited to: citric acid, tartrate salts, phthalate salts, borate salts, tris(hydroxymethyl)aminomethane (Tris-HCl), EDTA and phosphate salts. In general the choice of the buffer is dependent on the desired pH range of the composition. By choosing the appropriate buffer the pH of the composition may be altered to values ranging from about 1 to 11. Preferably the pH of the composition is maintained between about 4 and 10 more preferably between about 5 and 8. In general buffering agents modify the morphology of the proteins. Aqueous solutions containing these and other buffering agents improve the immunohistochemical staining ability of tissue samples to a greater extent than de-ionized water. The staining enhancement of tissue samples varies with the pH of the solution. In general, most tissue samples show the most enhancement at pH values between 5 and 8. Some tissue samples, however, do not show significant improvements at these pH levels.

The preferred buffers for a high pH (about 10) are ethanolamine (sigma #E9508), diethanolamine (DEA) (sigma #D068 1) and DEA-tris.

The composition may optionally include a dye or other substances that do not significantly contribute to the function of the composition. These substances are typically added to allow easy identification of the composition or to improve the odor of the composition.

According to a preferred embodiment, the composition is an aqueous solution which includes (a) a removing agent and (b) a tissue activating agent. The composition may optionally include a dye.

In a preferred embodiment, the composition is an aqueous solution which includes (a) up to about 25 percent by volume of SIMPLE GREEN and (b) up to about 10 percent by weight of citric acid and alkaline citrate salts. In a more preferred embodiment the composition is an aqueous solution which includes (a) about 1.85 percent by volume of SIMPLE GREEN, (b) about 0.3 percent by weight of trisodium citrate [dehydrate] dihydrate; and (c) sufficient concentrated hydrochloric acid to obtain a pH of about 5.96 to 6.04.

The composition, as described in previous embodiments, may be used to enhance the immunohistochemical staining ability of formalin-fixed embedded tissue samples. Tissue samples are preferably prepared by soaking the tissue in a buffered formalin or other fixative solution. After soaking for the appropriate time, the tissue sample is preferably dehydrated in ethanol, cleared using xylenes and embedded into paraffin blocks. The embedded tissue is preferably cut into sections up to about 5 micron sections; more preferably into about 3 micron sections. The tissue sample may be mounted onto a positively charged slide. The tissue sample is preferably mounted onto a poly-L-lysine coated slide. Poly-L-lysine is a positively charged, high molecular weight polymer of the amino acid lysine which, when coated onto a microscope slide, tends to act as a tissue adhesive bonding the tissue to the slide. The use of a tissue adhesive may be necessary to prevent the detachment of the tissue sample from the slide. After the samples have been mounted they may be dried for at least one hour at a temperature of about 58° C.

The mounted samples may then be contacted with a composition, prepared according to the previously described embodiments, and heated to a temperature of at least about 80° C. for a time period of at least about 10 minutes. The samples may be contacted with the composition by submersing a portion of the tissue sample within the composition. The samples are preferably substantially submerged within the composition. Heating may be accomplished by a number of heating devices including, but not limited to: autoclaves, pressure cookers, water baths, microwave ovens, and steam heating. In general it is preferred that the slides are heated to a temperature of at least 80° C. for a time period of at least 50 minutes; more preferably the slides are heated at least about 100° C. for a time period of at least about 30 minutes; more preferably still the slides are heated at a temperature of at least about 110° C. for a period of at least about 20 minutes. The slides may be heated at atmospheric pressure. When a pressure cooker is used as the heating source the slides are preferably heated to a temperature up to about 120° C. and a pressure of up to about 2 atmospheres.

The heating is preferably sustained for a time such that the samples also become substantially hydrated. During the embedding process the water in the tissue samples is typically removed by washing the tissue samples in an alcohol. To perform an immunohistochemical staining procedure upon the tissue samples it is preferred that the tissue is substantially saturated in water. These hydrated tissue samples typically exhibit improved immunohistochemical staining over unhydrated tissue samples.

After the slides have been heated in the composition they may be washed with an appropriate buffer solution to remove composition remaining on the slide. Alternatively, after the slides have been heated in the composition, they may be removed and washed with a second composition prepared according to the previously described embodiments. The second composition may include the same components as the initial composition. The second composition may be at least at room temperature. Preferably, the second composition is heated to a temperature of at least about 90° C. before the slides are contacted with the second composition. After contacting the slides with the second composition for about 5 minutes the slides may be additionally washed with an appropriate buffer solution to remove any of the composition remaining on the slide. The tissue samples may be stained at this point according to standard immunohistochemical staining protocols.

Examples of the composition and method will now be described in more detail. These examples are merely illustrative of the composition and method of the invention and are not intended to be limiting.

EXAMPLES

Exp. #1 Preparation of the Tissue Enhancing Composition

A buffered solution was prepared by dissolving the trisodium citrate dihydrate (2.9 g, 0.01 moles) in de-ionized water (1000 mL). Approximately 9 drops of concentrated hydrochloric acid were added to the solution. The pH of the solution was then determined. If the pH value was greater than 6.04, additional drops of concentrated hydrochloric acid were added until the pH dropped below 6.04. If the pH was below 5.96, drops of a 4N potassium hydroxide solution were added until the pH was greater than 5.96. The final pH of the solution was adjusted to between about 5.96 and 6.04.

To the buffered solution prepared as described above was added 18.5 mL of SIMPLE GREEN (Sunshine Makes Inc., Huntington Harbor, Calif.). The pH of the resulting solution was adjusted by addition of concentrated hydrochloric acid or 4N potassium hydroxide as needed to obtain a pH of about 5.96 to 6.04. The resulting tissue enhancing composition may be used to enhance the immunohistochemical staining of tissue samples.

Ex. #2. Method for the Preparation of Tissue Samples for Staining

Formalin-fixed, Paraffin-embedded tissues were cut into 3 micron sections and placed on positively charged slides ploy-L-lysine slides. The sections were dried for 1 hour at a temperature of 58° C. The sections were then placed in a TISSUE-TEK staining dish (Miles Inc., Elkhart, Ind. #4457) and sufficient Tissue Enhancing Composition, prepared as descried above, was added such that the tissue samples were substantially submerged within the solution. A second TISSUE-TEK staining dish was filled with a similar amount of Tissue Enhancing Composition. A pressure cooker (Presto Super Six Pressure Cooker #01263, National Presto Industries, Eau Claire, Wis.) was filled with tap water to a depth of approximately 1 inch. Both the TISSUE-TEK dish containing slides and Tissue Enhancing Composition, and the dish with only Tissue Enhancing Composition, were placed within the pressure cooker and the pressure cooker was sealed. The pressure cooker was heated on an electric burner until the temperature reached approximately 120° C. at a pressure of about 2 atm. Once these conditions were reached the pressure cooker was heated for an additional 10 minutes. After this time the pressure cooker was removed from the electric burner and partially cooled. The pressure was vented and the TISSUE-TEK dishes were removed. The slides were then removed from the first TISSUE-TEK dish and transferred to the second TISSUE-TEK dish, which contained hot Tissue Enhancing Composition. An IHC wash buffer was prepared by dissolving a Phosphate Buffered Saline with Tween 20 packet (Sigma Chemical Co., St. Louis, Mo. #P-3563) in IL of deionized water. The pH of the IHC wash buffer was adjusted to between 7.1 to 7.3 by addition of concentrated hydrochloric acid or 4N potassium hydroxide. After five to ten minutes the slides were removed and washed with an IHC wash buffer. IHC wash buffer may be obtained from Cell Marque Corp., Austin, Tex.

Exp. #3 Immunohistochemical Staining of the Tissue Samples

The staining of tissue samples is detailed in the Cell Marque 1998 and 2000 Products and Reference Guide, which are incorporated by reference as if fully set forth herein. Tissue sections on slides (prepared as described above) were treated with a solution of excess antibody for an appropriate amount of time, such time varying depending on the antibody and the protocol being used. The slides were rinsed with an IHC wash buffer. The slides were placed in a Peroxide Block solution for 10 minutes. After this time the slides were rinsed with IHC wash buffer The slides were then placed in a Biotinylated Link solution for 10 minutes at room temperature. After this time the slides were rinsed with IHC wash buffer. The slides were then placed in a Label solution for 10 minutes at room temperature. The Label solution enhances the sensitivity of the antibodies toward the chromogen. After this time the slides were again washed in an IHC wash buffer. The slides were placed in Chromogen solution for 10 minutes at room temperature. After this time the slides were removed and rinsed with de-ionized water. The slides were then placed in hematoxylin counterstain for 30 seconds at room temperature. The slides were finally rinsed with IHC wash buffer and following an appropriate mounting procedure a coverslip is placed over the tissue samples. All of the above mentioned solutions were obtained from Cell Marque Corp., Austin, Tex.

Exp. #4. Evaluation of the Staining Ability

The formalin-fixed, Paraffin-embedded tonsil tissue samples were treated with two compositions in the manner described in Experiment 2. The first composition (Composition 1) was prepared by dissolving the trisodium citrate dihydrate (2.9 g, 0.01 moles) in de-ionized water (1000 mL). The pH of the resulting solution was adjusted by addition of concentrated hydrochloric acid or 4N potassium hydroxide as needed to obtain a pH of about 5.96 to 6.04. The second composition (Composition 2) was the Tissue Enhancing Composition described in Exp. #1. The tissues were stained according to the method of Exp. #3 with a variety of antibodies (listed in Table 1) and the qualitative staining ability of the tissues was noted. The staining ability of the tissue samples treated in Composition 1 was compared to the staining of tissue samples treated in Composition 2. Staining was ranked on a scale of (−) to (+++++) where (−)=no staining; (+)=focal and weak staining; (++)= weak staining of a moderate number of cells; (+++)= moderate staining of most cells; (++++)=strong staining of cells; (++++)=very intense staining combined with excellent morphology and lack of any background staining.

TABLE 1

| ANTIBODIES | COMPOSITION 1 | COMPOSITION 2 |
|---|---|---|
| Actin, Muscle Specific, HHF35 | ++++ | +++++ |
| Actin, Smooth Muscle, 1A4 | +++++ | +++++ |
| AFP, Polyclonal | ++++ | +++++ |
| B-Cell, MB2 | ++++ | +++++ |
| bcl-2, 100/05 | ++ | +++++ |
| CA-125, OC125 | ++++ | +++++ |
| CD3, Polyclonal | +++++ | +++++ |
| CD5, 4C7 | ++++ | +++++ |
| CD8, C8/144B | +++ | +++++ |
| CD15, Leu-M1 | ++++ | +++++ |
| CD20, L-26 | ++++ | +++++ |
| CD23, 1B12 | +++ | +++++ |
| CD30, Ber-H2 | +++ | +++++ |
| CD31, JC/70A | ++ | ++++ |
| CD34, QBEnd/10 | ++++ | +++++ |
| CD43, DF-T1 | +++++ | +++++ |
| CD45, Bra55/2 | ++++ | ++++ |
| CD45RO, UCHL-1 | +++++ | +++++ |
| CD57, NK1 | ++++ | +++++ |
| CD68, KP1 | +++++ | +++++ |
| CD74, LN2 | +++++ | ++++ |
| CDw75, LN1 | ++ | ++++ |
| CD79a, HM57 | +++ | +++++ |
| CD99, MIC-2, HM57 | +++ | +++++ |
| Chromogranin A, LKH10 | +++++ | +++++ |
| Cytokeratin 7, K72 | ++++ | +++++ |
| Cytokeratin 8, 18, 19, 5D3 | + | +++ |
| Cytokeratin, 34betaE12 | ++++ | +++++ |
| Cytokeratin, 35betaH11 | +++ | ++++ |
| Cytokeratin Cocktail, AE1/AE3 | +++ | +++++ |
| DBA-44, DBA-44 | ++++ | +++++ |
| Desmin, D33 | ++++ | +++++ |
| EBV, CS1-4 | +++++ | +++++ |
| ER, 6F11 | +++ | +++++ |
| GFAP, G-A-5 | ++++ | +++++ |
| Hepatitis C, TORDJI-22 | +++ | +++++ |
| HSV I & II, 045-A/1930-B | + | +++++ |
| bCG, Polyclonal | +++++ | +++++ |
| Kappa, L1C1 | + | +++++ |
| Lambda, HP6054 | + | +++++ |
| Melanoma, HMB45 | ++++ | +++++ |

TABLE 1-continued

| ANTIBODIES | COMPOSITION 1 | COMPOSITION 2 |
|---|---|---|
| Myleine Basic Protein, Polyclonal | +++++ | +++++ |
| Neurofilament, BF.10 | ++++ | +++++ |
| NSE, E27 | ++++ | +++++ |
| P53, D07 | ++++ | +++++ |
| PLAP, Polyclonal | +++ | ++++ |
| PR, hPRa3 | ++++ | +++++ |
| PSAP, PASE/4LJ | +++ | +++++ |
| S-100, 4C4.9 | ++++ | +++++ |
| Vimentin, V9 | +++++ | +++++ |

A control sample was tested in which a formalin-fixed, tonsil tissue embedded in paraffin was heated in Composition 1 without any prior deparaffinization step. This tissue sample showed no staining in the presence of a variety of antibodies.

In addition to the results shown above, additional tests were performed using breast, prostate, thyroid, appendix, brain, lymph, skin, pancreas, colon, muscle bone marrow, and placenta tissue. Staining with these tissue samples also showed that the use of Composition 2 improved staining of these embedded tissue samples without any prior removal of the embedding medium. It should be noted that the samples treated with Composition 1 were deparaffinized prior to treatment, but the samples treated with Composition 2 were not deparaffinized prior to treatment. The use of a composition prepared according to the above embodiments, such as Composition 2, allows this deparaffinization step to be omitted and yet staining of the tissue samples of comparable or even better quality may be obtained.

While the above Exp. #4 was performed on tissue samples that have been heated in the above mentioned compositions, it should be appreciated that the reactions may also be performed at temperatures lower than described in the experiments. The treatment temperature may effect the rate of the tissue enhancing process. The rate of embedding medium removal, enhancement of the tissue sample, and rehydration of the tissue sample may all increase as the temperature is elevated. When the temperature is lowered, e.g. when the reaction is run at room temperature, the rate of these three processes may also be lowered. The lowering in rate may not have an effect on the enhancement of the tissue sample toward immunohistochemical staining, but may have an effect on the time period required for such enhancement to occur.

The use of a composition prepared according to the above embodiments may allow three steps to be performed in a substantially simultaneous manner: (i) removal of the embedding medium from the tissue; (ii) improvement of the immunohistochemical staining of the tissue in comparison to tissue that has not been contacted with the composition; and (iii) rehydration of the tissue sample. The importance of each of these three steps may be illustrated in Exp. #4. When a composition that only performs two of the three steps mentioned above is used, enhancement of the tissue samples may not be as pronounced as when all three steps are performed by a single composition. When Paraffin-embedded tissue samples are treated with a composition including only a tissue activating agent in water, little or no staining is seen. By removing the paraffin embedding medium prior to treating the tissue sample with a composition including a tissue activating agent in water, the staining may be improved, as shown for Composition 1 in Table 1. When a solution including a removing agent, a tissue activating agent, and a removing enhancer is used with water, e.g. Composition 2, the results in Table 1 show enhancement of the tissue samples that is substantially improved over the use of Composition 1 on deparaffinized samples. These results show that composition 2 not only allows the three steps to be performed simultaneously, but also may show a significant improvement over the samples that have been deparaffinized and then treated with Composition 1. Exp. #4 shows the importance of the removing agent and/or removing agent enhancers with respect to both removal of the embedding medium and enhancement of the staining of the tissue samples.

ADDITIONAL TRIALS

These additional trials were performed with Vimentin antibodies, the tissue was human tonsil and they were scored based on the following (see also preamble to table 2): intensity 1 to 4+, 1 being the weakest, 4+strongest; and, background 1 to 4, 1 being the cleanest, 4 dirtiest.

A stock solution of 1 millimolar EDTA was used. This stock solution was prepared when a first reagent was prepared from 186.1 grams EDTA and 1 liter of de-ionized water (adjusted to the pH of 8). 200 milliliters of this solution was then added to 30 gallons of de-ionized water to produce of 1 millimole EDTA stock solution, which was used as the tissue activating agent in all the following trials. It is noted that the 0.5 millimole EDTA solution was adjusted to pH 8 by the addition of hydrochloric acid or potassium hydroxide as necessary.

In what follows, the staining results are described using a scoring system that is described at the beginning of Table 2.

Trials 1A to 1D, emulsifier #1, Igepal CA-630.

Trial 1A was run with 0.1 percent Igepal and 100 milliliters of 1 millimolar EDTA. Results were approximately 4/1.

Trial 1B was run the same as 1A except with a 0.5 percent Igepal solution yielding similar results.

Trial 1C was run at 0.1% Igepal, 100 milliliters of EDTA 1 millimolar and DEA 50 millimolar to yield a stain score 4+/1.

Trial 1D was run the same as Trial 1C except 0.5 percent Igapel and the results were about the same as Trial 1C.

The second series of trials were run with emulsifier #2, Tween 20. These trials are set forth below as 2A through 2D.

Trial 2A was run with Tween 20 at a 0.1 percent concentration with 100 milliliters of EDTA 1 millimolar to yield a stain score of 2/1.

Trial 2B was run as Trial 1A except with a 0.5 percent Tween 20 solution and yielded a stain score of 2/1.

Trial 2C was run as Trial 2A except with the addition of DEA 50 millimolar to yield a stain score of 2+/1.

Trial 2D was run the same as Trial 2C except Tween 20 was used at 0.5 percent concentration and yielded a stain score of 3/1.

The third series of Trials were run with a emulsifier #3, Brij 35. Those trials are set forth below as Trial 3A to 3D.

Trial 3A was run with a 0.1 percent Brij 35 solution having 100 milliliters of EDTA 1 millimolar to yield a stain score of 2+/1.

Trial 3B was run as Trial 3A with Brij 35 except at a 0.5 percent concentration to yield a stain score of 2/1.

Trial 3C was run as Trial 3B except with the addition of DEA 50 millimolar to yield a stain score of 0.

Trial 3D was run as Trial 3C except 0.5 percent Brij 35 and yielded a stain score of 0.

A fourth set of trials were run with emulsifier #4, Tween 80. They are set forth below as 4A to 4C.

Trial 4A used 0.1 percent Tween 80 and EDTA 100 milliliters of 1 millimolar to yield a stain score of 2/1.

Trial 4B was run as Trial 4A except the use of 0.5 percent Tween 80 to result in a stain score of about 2/1.

Trial 4C was run with 0.1 percent Tween 80, 100 milliliters EDTA 1 millimolar and 50 millimolar DEA to yield a stain score of 2/1.

Trial 4D was run as Trial 4C except with the use of 0.5 percent Tween 80 and resulted in a stain score of 2/1.

A fifth emulsifier was run, here Brij 99 as set forth in Trials 5A to 5D below.

Trial 5A was run with 0.1 percent Brij 99 and 100 milliliters of EDTA 1 millimolar and yielded a stain score of 2/1.

Trial 5B was run as Trial 5A except with 0.5 percent Brij 99 solution and resulted in a stain score of 2/1.

Trial 5C. was run with a 0.1 percent Brij 99 solution, 100 milliliters EDTA 1 millimolar and DEA 50 millimolars to yield a stain score of 2/1.

Trial 5D was run as Trial 5C except with 0.5 percent Brij 99 concentration to yield a stain score of 2/1.

A sixth emulsifier was also run, here Triton X 100. The results are set forth below in Trials 6A to 6D.

Trial 6A was run with 0.1 percent Triton X 100 with 100 milliliters of EDTA 1 millimolar to yield a stain score of 2/1.

Trial 6B was run as Trial 6A except with 0.5 percent Triton X 100 solution to yield a stain score of 2/1.

Trial 6C was run with 0.1 percent Triton X 100, 100 milliliters EDTA 1 millimolar and DEA 50 millimolars to yield a stain score of 2/1.

Trial 6D was run as Trial 6C except using 0.5 percent Triton X 100 yielding a stain score of 2/1.

An additional emulsifier was run in a seventh set of Trials, set forth below as Trial 7A to 7D. The emulsifier was CD TAB.

Trial 7A was run at 0.1 percent CD TAB, 100 milliliters EDTA 1 millimolar to yield a stain score of 2/1.

Trial 7B was run as Trial 7A except at 0.5 percent CD TAB to yield a stain score of 2/1.

Trial 7C was run as Trial 7A except adjusted to DEA 50 millimolars to yield a stain score of 2/1.

Trial 7D was run as Trial 7C except as 0.5 percent CD TAB to yield a stain score of 2/1.

Heat and water alone, applicants have found, are insufficient for one step deparaffinization, unmasking and rehydration. Aqueous solutions of emulsifying agents, such as those set forth herein and known unmasking agents such as EDTA and Citrate Buffer at known concentrations, work effectively in one step, to prepare a Paraffin-embedded, fixed tissue, for staining. The typical three step method of paraffin removal, rehydration and then unmasking may be reduced to a single step of pretreating the Paraffin-embedded fixed tissue in a single liquid composition set forth herein.

One could select well known unmasking agents used at known concentrations and combine them with applicants paraffin removal solution to effectively restore antigencity of a Paraffin-embedded fixed tissue in one heating step.

In another embodiment of the invention the removing agent acts to remove the embedded medium by the process of emulsification.

These compositions will work successfully on tissues fixed with fixatives other than formalin, for example B5, alcohol fixatives, Zinc formalin, PREFER™ and Bouin's.

TABLE 2

Scoring of Stains

| | No Un-masking | Protease | Citrate Buffer | Declere | Trilogy |
|---|---|---|---|---|---|
| ACTH Polyclonal | 3/1 | 3/1 | 4/1 | 4/1 | 4+/1 |
| Actin, Muscle Specific 1A4/5C5.F8.C7 | 3+/1 | 3+1+ | 4/2 | 4/1 | 4+/1 |
| Actin, Smooth Muscle 1A4 | 4/1 | 3/1 | 4+/1 | 4+/1 | 4+/1 |
| Adenovirus 20/11/2/6 | 0 | 4+/1 | 3/1 | 3+/1 | 3/1 |
| AFP (Alpha Fetoprotein) Polyclonal | 4+/1 | 3/1 | 4/1 | 4/1 | 4+/1 |
| Alpha-1-Antichymotryspin Polyclonal | 3/1 | 4/1+ | 4+/1 | 4/2 | 4+/2 |
| Alpha-1-Antitrypsin Polyclonal | 3/1 | 4/1+ | 4+/1 | 4/1 | 4/1 |
| B-Cell MB2 | 2+/1 | 0 | 4+/1 | 4+/1 | 4+/1 |
| BCA-225 (Breast Carcinoma) cu-18 | 3/1 | 4+/1 | 4/1 | 4/1 | 4/1 |
| bcl-2 124 | 0 | 0 | 4+/1 | 4/1 | 4/1 |
| c-erbB-2 (Her2/NU) CB-11 | 2/1 | 2/1 | 4/1 | 4/1 | 4+/1 |
| CA15-3 DF3 | 3/1 | 4+/1 | 4/1 | 4/1 | 4/1 |
| CA19-9 121SLE | 4/1 | 4/1 | 4+/1 | 4+/1 | 4+/1 |
| CA-125 OC125 | 0 | 3/1 | 4/1 | 4/1 | 4+/1 |
| Catclionin Polyclonal | 4/1+ | 3/1 | 4/1 | 4/1 | 4/1 |
| Calretinin Polyclonal | 2/1 | 3/1 | 4/1 | 4/1 | 4+/1 |
| CD3 Polyclonal | 0 | 3/1 | 4/1 | 4/1 | 4+/1 |
| CD5 4C7 | 0 | 0 | 4+/1 | 4/1 | 4+/1 |
| CD8 C8/144B | 0 | 0 | 4+/1 | 4/1 | 4+/1 |
| CD10 270 | 0 | 0 | 4/1 | 4/1 | 4+/1 |
| CD15 MMA | 3/1 | 3/1 | 4+/1 | 4+/1 | 4+/1 |
| CD20 L-26 | 3/1 | 3/1 | 4+/1 | 4+/1 | 4+/1 |
| CD23 1B12 | 0 | 0 | 4/1 | 4/1 | 4+/1 |
| CD30 Ber-H2 | 2/1 | 3/1 | 4+/1 | 3+/1 | 4+/1 |
| CD31 JC/70A | 0 | 2+/1 | 3/1 | 4/1 | 4+/1 |
| CD34 QBEnd/10 | 3+/1 | 2/1 | 4/1 | 4/1 | 4+/1 |
| CD43 MT1 | 4+/1 | 4/1 | 4/1 | 4/1 | 4/1 |
| CD45 (LCA) 2611/PD7/26 | 4/1 | 2/1 | 4/1 | 4/1 | 4+/1 |
| CD45R MB1 | 2/1 | 0 | 4/1 | 4/1 | 4+/1 |
| CD45RA MT2 | 3/2 | 3/2 | 3/1 | 4/1 | 3/1 |
| CD45RO UCHL-1 | 4/1 | 2/1 | 4+/1 | 4/1 | 4+/1 |
| CD56 123C3.D5 | 0 | 0 | 4/1 | 4/1 | 4+/1 |
| CD57 NK1 | 3+/1+ | 4/1+ | 4/1 | 4/1 | 4/1 |
| CD68 KP1 | 0 | 3/1 | 4/1 | 4/1 | 4+/1 |
| CD74 LN2 | 0 | 0 | 4+/1 | 4/1 | 4/1 |
| CDw75 LN1 | 0 | 3/1 | 4+/1 | 4/1 | 4/1 |
| CD79a JCB117 | 0 | 0 | 3+/1 | 4/1 | 4+/1 |
| CD99 (MIC.2) H036-1.1 | 0 | 0 | 4+/1 | 4/1 | 4+/1 |
| CEA CMO1 | 3/1 | 4/1 | 4+/1 | 4/1 | 4+/1 |
| Chromogranin A LK2H10 | 4/1 | 0 | 4+/1 | 4+/1 | 4+/1 |
| Collagen Type-IV CIV22 | 2/1 | 4+/1 | 4/1 | 4/1 | 4+/1 |
| Cyclin D1 Polyclonal | 2/1 | 3/1 | 4+/1+ | 4/1 | 4+/1 |
| Cytokgratin 7 K72 | 3/1 | 4+/1 | 4/1 | 4/1 | 4+/1 |
| Cytokeratin 8,18,19 SD3 | 0 | 4+/1 | 4/1 | 4/1 | 4+/1 |
| Cytokeratin 20 Ks20.8 | 0 | 4+/1 | 3/1 | 4/1 | 4+/1 |
| Cytokeratin 34betaE12 | 2/1 | 4/1 | 4/1 | 4/1 | 4+/1 |
| Cytokeratin 35betaH11 | 2/1 | 4+/1 | 3/1 | 3/1 | 3+/1 |
| Cytokeratin Cocktail AE1/AE3 | 2/1 | 4/1** | 4/1 | 4+/1 | 4+/1 |
| Cytokeratin, HMW AE3 | 2/1+ | 0 | 4/1+ | 4/1 | 4/1 |
| Cytokeratin, LMW AE1 | 2/1- | 4/1 | 4/1 | 4/1 | 4/1 |
| CMV DDG9/CCH2 | 0 | 4+/1 | 3/1 | 4/1 | 4/1 |
| Desmin D33 | 3/1 | 0 | 4+/1 | 4+/1 | 4+/1 |
| ECadherin ECH-6 | 0 | 0 | 3/1 | 4/1 | 4/1 |
| EBV CS1-4 | 3/1 | 4/1 | 3+/1 | 4/1 | 3+/1 |
| EMA E29 | 4/1 | 4/1 | 4+/1 | 4/1 | 4+/1 |
| ER 1D5 | 0 | 0 | 4/1 | 4+/1 | 4+/1 |
| Factor VIII-R Ag. Polyclonal | 3/1+ | 4+/1 | 4/1 | 4/1 | 4+/1 |
| Fascin 55k-2 | 4+/1+ | 0 | 4+/1+ | 4+/1 | 4+/1 |
| FSH Polyclonal | 2/1 | 3/1 | 4/1 | 4/1 | 4/1 |
| Gastrin Polyclonal | 2/1 | 2+/1 | 4/1 | 4/1 | 4+/1 |
| GFAP G-A-5 | 4/1 | 4/1 | 4+/1 | 4+/1 | 4+/1 |
| GH Polyclonal | 3/1 | 4/1 | 4/1 | 4/1 | 4/1 |
| Glucagon Polyclonal | 0 | 0 | 3/1 | 4/1 | 4+/1 |
| Helicobacter Pylori Polyclonal | 0 | 4/1 | 4/1 | 4/1 | 4+/1 |
| HBcAg (Hepatitis B Core) Polyclonal | 4/1+ | 4/1 | 4/1+ | 4/1 | 4+/1 |
| HBsAg (Hepatitis B Surface) S1-210 | 4/1 | 4+/1 | 4+/1 | 4/1 | 4+/1 |
| HSV I & II (Herpes Simplex) Polyclonal | 3/1+ | 3/1* | 4+/1 | 4/1 | 4+/1 |
| hCG Polyclonal | 2+/1 | 4+/1 | 4/1 | 4/1 | 4/1 |
| IgA Polyclonal | 4/1 | 4+/1+ | 4/1 | 4/1 | 4/1 |
| IgM Polyclonal | 4/1 | 4+/1+ | 4/1 | 4/1 | 4/1 |
| Inhibin R1 | 0 | 0 | 4/1 | /1 | 4/1 |
| Insulin Polyclonal | 3/1 | 4+/1 | 4+/1 | 4/1 | 4+/1 |
| Kappa | 0 | 4+/1 | 4/1 | 3/1 | 4/1 |

-continued

| | No Un-masking | Protease | Citrate Buffer | Declere | Trilogy |
|---|---|---|---|---|---|
| L1C1 | | | | | |
| Ki-67 | 0 | 0 | 4/1 | 4/1 | 4/1 |
| MIB-1 | | | | | |
| Lambda | 0 | 4+/1 | 4/1 | 4/1 | 4+/1 |
| HP6054 | | | | | |
| LH | 3/1 | 4+/1 | 4/1 | 4/1 | 4+/1 |
| Polyclonal | | | | | |
| Lysozyme | 3/1 | 4/1 | 4+/1 | 4/1 | 4+/1 |
| Polyclonal | | | | | |
| Macrophage | 2/1 | 3+/1 | 3/1 | 4/1 | 4+/1 |
| HAM-56 | | | | | |
| Mart-1 | 0 | 0 | 3/1 | 3+/1 | 4/1 |
| M2-7C10 | | | | | |
| Melanoma | 4+/1 | 3/1 | 4/1 | 4+/1 | 3/1 |
| HMB45 | | | | | |
| Myeline Basic Protein | 2/1 | 4/1 | 4/1 | 4/1 | 4/1 |
| Polyclonal | | | | | |
| Myeloperoxidase | 4/2 | 4+/2 | 4/1 | 4+/1 | 4+/1 |
| Polyclonal | | | | | |
| Myogenin | 0 | 0 | 3/1 | 4/1 | 4/1 |
| F5D | | | | | |
| Myoglobin | 0 | 0 | 4+/1 | 4+/1 | 4+/1 |
| Polyclonal | | | | | |
| Neurofilament | 3+/1 | 3+/1 | 4+/1 | 4+/1 | 4+/1 |
| 2F11 | | | | | |
| NSE | 3/1 | 2/1* | 4/1+ | 4+/1 | 4+/1 |
| E27 | | | | | |
| p53 Suppressor Gene | 2/1 | 0 | 4/1 | 4+/1 | 4+/1 |
| D07 | | | | | |
| Papillomavirus (HPV) | 0 | 0 | 4+/1 | 4/1 | 4/1 |
| Polyclonal | | | | | |
| Parvovinus B19 | 0 | 0 | 4+/1 | 4+/1 | 4+/1 |
| B19,R92F6 | | | | | |
| PLAP | 0 | 0 | 4/1 | 4+/1 | 4+/1 |
| NB10 | | | | | |
| *Pneumocystis caninii* | 3+/1 | 3/1 | 2+/1 | 3/1 | 3/1 |
| 3F6 | | | | | |
| PR | 0 | 0 | 4/1 | 4/1 | 4+/1 |
| hPRa2 + 3 | | | | | |
| Prolactin | 0 | 3/1 | 4/1 | 4+/1 | 4+/1 |
| Polyclonal | | | | | |
| PSA | 4/2 | 3/1 | 4+/1 | 4/1 | 4+/1 |
| Er-Pr8 | | | | | |
| PSAP | 4+/2 | 2/1 | 4/1 | 4/2 | 4/1 |
| PASE/4LJ | | | | | |
| S-100 | 3+/1 | 3/1* | 4+/1 | 4+/1 | 4+/1 |
| 4C4.9 | | | | | |
| Smoth Muscle Myosin, | 0 | 0 | 3/1 | 4/1 | 4+/1 |
| HC SMMS-1 | | | | | |
| Somatostatin | 0 | 0 | 4+/1 | 4+/1 | 4+/1 |
| Polyclonal | | | | | |
| Synaptophysin | 0 | 0 | 4+/1 | 4+/1 | 4+/1 |
| Polyclonal | | | | | |
| TAG-72 | 3+/1 | 4/1 | 4/1 | 4/1 | 4+/1 |
| B72.3 | | | | | |
| TdT | 0 | 2/1 | 4/1 | 4/1 | 4/1 |
| Polyclonal | | | | | |
| Thyroglobulin | 2+/1 | 3/1* | 4+/1+ | 4/1 | 4/1 |
| 2H11/6E1 | | | | | |
| Toxoplasma Gondli | 2/1 | 3+ | 4/1 | 4+/1 | 4+/1 |
| Polyclonal | | | | | |
| TSH | 3/1 | 4/1 | 3/1 | 4/1 | 4/1 |
| Polyclonal | | | | | |
| TTF-1 | 0 | 0 | 4/1 | 4/1 | 3/1 |
| 8G7G3/1 | | | | | |
| Ulex Europeaus | 3/1 | 4/1 | 4/1 | 4+/1 | 4+/1 |
| Polyclonal | | | | | |
| Vimentin | 0 | 0 | 4+/1 | 4+/1 | 4+/1 |
| V9 | | | | | |

Applicant has compared traditional pretreatments with Declere (the SIMPLE GREEN formulation) and Trilogy™ (Trial A4) for immunohistochemical stains of the following clones of antibodies on formalin-fixed, paraffin-embedded tissues. The stains were performed using a Ventana ES immunostainer with antibody incubation time set at 32 minutes and were scored for intensity and for background. The table below lists Applicant's observations.

The number to the left of the slash represents the intensity of the stained target antigen (4 being the most intense, 1 being the least intense.) A plus sign is used to augment the value of the score and indicates incremental intensity. The higher this number is, the more intense the stained target antigen and the more desirable the result.

The number to the right of the slash represents the intensity of the background or "noise"(4 being the most intense, 1 being the cleanest.) A plus sign is used to augment the value of the score and indicates incremental intensity. The lower this number is, the less pronounced the background and the more desirable the result.

A zero indicates no staining. An asterisk (*) indicates that the results for this pretreatment method varied due to the variablility of fixation. The double asterisk (**) indicates that the staining result of the protease pretreated cocktail is not reliable since the AE3 component did not stain when run separately with this method.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials maybe substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A composition for enhancing antigenicity of a formaldehyde-fixed, paraffin-embedded, tissue, the composition being a buffered solution comprising:
   about 0.01 moles of trisodium citrate dihydrate, about 1000 milliliters of water and about 18.5 milliliters of a mixture having by weight about 5.8% ethylene glycol monobutyl ether, about 3.75% nonylphenol ethoxylate, about 1.5% tetrapotassium pyrophosphate and about 88.95% water; and
   the composition having a pH between about 5.96 and about 6.04.

2. An aqueous composition for enhancing antigenicity of a formaldehyde-fixed, paraffin-embedded, slide-mounted tissue, the composition having a pH between about 5.96 and about 6.04 and comprising:
   greater than 0% and up to about 25% by volume of a mixture having by weight about 5.8% ethylene glycol monobutyl ether, about 3.75% nonylphenol ethoxylate, about 1.5% tetrapotassium pyrophosphate and about 88.95% water; and
   greater than 0% and up to 10% by weight of citric acid and alkaline citrate salts.

3. A method for enhancing antigenicity using the composition of claim 1 or 2, including the steps of:
   contacting a formalin-fixed, paraffin-embedded tissue with the composition and heating to a temperature of at least 80° C. for a time sufficient so that paraffin is removed from the tissue into the heated composition contacting the tissue and the tissue becomes substantially hydrated;

thereafter removing the tissue from contact with the composition including washing the tissue to remove residual composition;

wherein the antigenicity of the contacted, heated, and washed tissue for immunochemical staining is enhanced over that of formalin-fixed, paraffin-embedded tissue not so contacted.

4. A method for enhancing immunochemical staining of a paraffin-embedded, formalin-fixed tissue with a single solution, the method comprising:

immersing said tissue for a period of at least about 10 minutes and a temperature of at least 80° C. in an aqueous, paraffin-removing, tissue-activating agent solution having a pH from about 2 to about 8, said solution containing greater than 0% and up to about 10% by weight of at least one surfactant capable of, upon heating, removing paraffin from the tissue in contact therewith and also containing at least one tissue activating agent selected from a buffer or a salt;

thereafter removing the tissue from the solution including washing the tissue to remove residual solution;

wherein the immunochemical staining of the immersed, heated, and washed tissue is enhanced over that of formalin-fixed, paraffin-embedded tissue not so immersed and heated.

5. The method of claim 4 where the solution has a pH of from 5 to 8.

6. The method of claim 4 where the surfactant is an aromatic hydrocarbon sulfonate salt.

7. The method of claim 4 where the surfactant is at least one of a cationic, anionic, amphoteric, or nonionic surfactant.

8. The method of claim 4 where the tissue activating agent is a metal salt.

9. The method of claim 4 where the tissue activating agent is at least one salt selected from the group consisting of aluminum chloride, sodium chloride, sodium fluoride, iron chloride, zinc sulfate, and lead thiocyanate.

10. The method of claim 4 where the tissue activating agent is a buffer.

11. The method of claim 4 where the tissue activating agent is at least one of a citrate salt, tartrate salt, phthalate salt, borate salt tris (hydroxymethyl) aminomethane ethylenediamine tetreactic acid or phosphate salt.

12. The method of claim 4 where the tissue activating agent is ethylenediamine tetreacetic acid.

* * * * *

(12) INTER PARTES REEXAMINATION CERTIFICATE (0243rd)
United States Patent
Aghassi et al.

(10) Number: US 6,649,368 C1
(45) Certificate Issued: Mar. 8, 2011

(54) COMPOSITION AND METHOD FOR TREATING TISSUE SAMPLES

(75) Inventors: Nora Betyousef Aghassi, Hot Spring, AR (US); Kim Franceschini, Austin, TX (US); Paul John Ardi, Hot Springs Village, AR (US)

(73) Assignee: Cell Marque Corporation, Austin, TX (US)

Reexamination Request:
No. 95/001,137, Jan. 13, 2009

Reexamination Certificate for:
Patent No.: 6,649,368
Issued: Nov. 18, 2003
Appl. No.: 09/515,283
Filed: Feb. 29, 2000

Related U.S. Application Data

(63) Continuation-in-part of application No. 08/957,098, filed on Oct. 24, 1997, now abandoned.

(51) Int. Cl.
*G01N 33/53* (2006.01)

(52) U.S. Cl. .................... 435/40.52; 435/5; 435/7.1; 435/7.32; 435/7.94; 435/7.95; 435/40.5; 436/503; 436/518

(58) Field of Classification Search .................... None
See application file for complete search history.

(56) References Cited

U.S. PATENT DOCUMENTS 6,451,551 B1  9/2002  Zhan et al.

OTHER PUBLICATIONS

Falkeholm, Lars (1996) Going Green: Using Water, Not Xylene, Laboratory Medicine 27(10): 638.

Hazelbag, Hans Marten et al. (1995) Immunostaining of Chain–Specific Keratins on Formalin–Fixed Paraffin–Embedded Tissues: A Comparison of Various Antigen Retrieval Systems Using Microwave Heating and Proteolytic Pre–Treatments, The Journal of Histochemistry and Cytochemistry 43(4): 429–437.

Wang, L.T., et al. (1996) Nested PCR–SSCP Assay for the Detection of p53 Mutations in Paraffin Wax Embedded Bone Tumours: Improvement of Sensitivity and Fidelity, Journal of Clinical Pathology: Molecular Pathology 49: M176–M178.

Werner, M., et al. (1996) Antigen Retrieval, Signal Amplification and Intensification in Immunohistochemistry, Histochemistry and Cell Biology 105:253–260.

*Primary Examiner*—Brenda Brumback

(57) ABSTRACT

Compositions and methods are described for enhancing the immunohistochemical staining of tissue samples. Compositions include a single solution, which includes at least one surfactant, adapted to remove an embedding medium of a tissue sample, rehydrate the tissue sample, and enhance the immunohistochemical staining of the tissue in relation to immunohistochemical staining of unreacted tissue. Methods include heating the tissue sample with the composition to enhance the immunohistochemical staining of the tissue.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 4-12 are cancelled.

Claims 1-3 were not reexamined.

\* \* \* \* \*